(12) United States Patent
Efremova et al.

(10) Patent No.: US 8,562,774 B2
(45) Date of Patent: Oct. 22, 2013

(54) METHOD OF FORMING A NONWOVEN FABRIC AND FASTENING SYSTEM THAT INCLUDE AN AUTO-ADHESIVE MATERIAL

(75) Inventors: Nadezhda V. Efremova, Neenah, WI (US); Bruce M. Siebers, Kimberly, WI (US); Lisha Yu, Appleton, WI (US); Christian L. Sanders, Decatur, GA (US); Gary D. Williams, Neenah, WI (US); Nicholas A. Kraft, Appleton, WI (US); Sheng-Hsin Hu, Appleton, WI (US); Jeffrey D. Lindsay, Appleton, WI (US); Fung-jou Chen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/226,752

(22) Filed: Sep. 7, 2011

(65) Prior Publication Data

US 2011/0315309 A1 Dec. 29, 2011

Related U.S. Application Data

(62) Division of application No. 11/260,356, filed on Oct. 27, 2005, now Pat. No. 8,034,430.

(51) Int. Cl.
*B32B 5/26* (2006.01)
*D04H 1/54* (2012.01)
*D04H 3/14* (2012.01)

(52) U.S. Cl.
USPC .......................................... 156/167; 156/181

(58) Field of Classification Search
USPC .............................................. 156/167, 181
See application file for complete search history.

(56) References Cited

U.S. PATENT DOCUMENTS

| 3,338,992 A | 8/1967 | Kinney |
| 3,341,394 A | 9/1967 | Kinney |

(Continued)

FOREIGN PATENT DOCUMENTS

| CA | 803714 A | 1/1969 |
| EP | 0235949 A1 | 9/1987 |

(Continued)

OTHER PUBLICATIONS

Further Official Letter received in EP Patent Application No. 06772059.9 dated Dec. 16, 2011.

(Continued)

*Primary Examiner* — Michael Tolin
(74) *Attorney, Agent, or Firm* — Armstrong Teasdale LLP

(57) ABSTRACT

In some embodiments, a nonwoven fabric includes a first web that is at least partially formed of extruded strands which include an auto-adhesive material. The nonwoven fabric is adapted to be bonded to another item that includes a similar auto-adhesive material. In other embodiments, a method of forming a nonwoven fabric includes extruding a plurality of strands that are formed of an auto-adhesive material. The method further includes routing the plurality of strands toward a moving support, depositing the plurality of strands onto the moving support, and then stabilizing the plurality of strands to form a web. In other embodiments, a fastening system includes a nonwoven fabric that has a web which is formed of a plurality of extruded strands that include an auto-adhesive material. The fastening system further includes a foam layer that has a surface with a plurality of free-standing struts that include a similar auto-adhesive material.

16 Claims, 7 Drawing Sheets

(56) References Cited

U.S. PATENT DOCUMENTS

| | | | |
|---|---|---|---|
| 3,423,266 A | 1/1969 | Davies et al. |
| 3,502,538 A | 3/1970 | Petersen |
| 3,502,763 A | 3/1970 | Hartmann |
| 3,542,615 A | 11/1970 | Dobo |
| 3,595,245 A | 7/1971 | Buntin et al. |
| 3,595,731 A | 7/1971 | Davies et al. |
| 3,649,436 A | 3/1972 | Buese |
| 3,676,242 A | 7/1972 | Prentice |
| 3,692,618 A | 9/1972 | Dorschner et al. |
| 3,704,198 A | 11/1972 | Prentice |
| 3,715,251 A | 2/1973 | Prentice |
| 3,745,587 A | 7/1973 | Bradley |
| 3,802,817 A | 4/1974 | Matsuki et al. |
| 3,849,241 A | 11/1974 | Butin et al. |
| 3,909,009 A | 9/1975 | Cvetko et al. |
| 3,921,221 A | 11/1975 | Zoephel |
| 3,922,455 A | 11/1975 | Brumlik |
| 3,935,046 A | 1/1976 | Kiernan et al. |
| 4,040,124 A | 8/1977 | Zoephel |
| 4,041,203 A | 8/1977 | Brock et al. |
| 4,068,036 A | 1/1978 | Stanistreet |
| 4,340,563 A | 7/1982 | Appel et al. |
| 4,342,808 A | 8/1982 | Langen et al. |
| 4,522,874 A | 6/1985 | Pommez |
| 4,608,047 A | 8/1986 | Mattingly |
| 4,692,618 A | 9/1987 | Klatt |
| 4,778,460 A * | 10/1988 | Braun et al. .................. 604/380 |
| 4,791,024 A | 12/1988 | Clerici et al. |
| 5,019,069 A | 5/1991 | Klemp |
| 5,019,072 A | 5/1991 | Polski |
| 5,085,655 A | 2/1992 | Mann et al. |
| 5,123,983 A * | 6/1992 | Marshall ....................... 156/167 |
| 5,176,669 A | 1/1993 | Klemp |
| 5,221,276 A | 6/1993 | Battrell |
| 5,294,482 A | 3/1994 | Gessner |
| 5,378,536 A | 1/1995 | Miller et al. |
| 5,389,438 A | 2/1995 | Miller et al. |
| 5,415,650 A | 5/1995 | Sigl |
| 5,425,987 A | 6/1995 | Shawver et al. |
| 5,503,908 A | 4/1996 | Faass |
| 5,518,795 A | 5/1996 | Kennedy et al. |
| 5,540,976 A | 7/1996 | Shawver et al. |
| 5,575,874 A | 11/1996 | Griesbach, III et al. |
| 5,636,414 A | 6/1997 | Litchholt |
| 5,647,864 A | 7/1997 | Allen et al. |
| 5,743,897 A | 4/1998 | Niihara et al. |
| 5,853,842 A | 12/1998 | Gallagher et al. |
| 5,888,335 A | 3/1999 | Kobe et al. |
| 5,912,059 A | 6/1999 | Jones et al. |
| 6,004,670 A | 12/1999 | Kobe et al. |
| 6,051,094 A | 4/2000 | Melbye et al. |
| 6,133,173 A * | 10/2000 | Riedel et al. .................. 442/400 |
| 6,171,985 B1 | 1/2001 | Joseph et al. |
| 6,180,205 B1 | 1/2001 | Tachauer et al. |
| 6,261,278 B1 | 7/2001 | Chen et al. |
| 6,419,667 B1 | 7/2002 | Avalon et al. |
| 6,503,855 B1 | 1/2003 | Menzies et al. |
| 6,524,294 B1 | 2/2003 | Hilston et al. |
| 6,562,167 B2 | 5/2003 | Coenen et al. |
| 6,595,977 B1 | 7/2003 | Luizzi et al. |
| 6,613,113 B2 | 9/2003 | Minick et al. |
| 6,896,843 B2 | 5/2005 | Topolkaraev et al. |
| 6,994,904 B2 | 2/2006 | Joseph et al. |
| 2002/0095130 A1 | 7/2002 | Seitter et al. |
| 2005/0096613 A1 | 5/2005 | Carper et al. |
| 2005/0148268 A1 | 7/2005 | Tai |
| 2005/0158567 A1* | 7/2005 | Carper et al. ................. 428/483 |
| 2005/0186387 A1 | 8/2005 | Gallant et al. |

FOREIGN PATENT DOCUMENTS

| | | |
|---|---|---|
| EP | 0528282 A2 | 2/1993 |
| EP | 1133967 A1 | 9/2001 |
| GB | 1217892 A | 12/1970 |
| JP | 03-167361 A | 7/1991 |
| JP | 09-249863 A | 9/1997 |
| KR | 10-0322360 | 6/2002 |
| KR | 10-2005-0072703 | 7/2012 |
| RU | 2240764 C2 | 11/2004 |
| RU | 2261078 C2 | 9/2005 |
| WO | 9201432 A1 | 2/1992 |
| WO | 9927875 | 6/1999 |
| WO | 0136011 A1 | 5/2001 |
| WO | 0243638 A2 | 6/2002 |
| WO | 2005044560 A1 | 5/2005 |

OTHER PUBLICATIONS

Wente, V. A., et al., "Manufacture of Superfine Organic Fibers", Naval Research Laboratory Report 4364 (111437), Corp Author(s): United States. Dept. of Commerce. Office of Technical Services.; Naval Research Laboratory (U.S.), (May 25, 1954),19 pgs.

Wente, Van A., "Superfine Thermoplastic Fibers", Industrial & Engineering Chemistry, 48(8), (Aug. 1956),1342-1346.

English translation of Chinese Office Action issued in related Chinese Application No. 200680039423.8, dated Aug. 2, 2010.

English Translation of Russian Office action in related Application No. 2008120559/04, Issued Sep. 22, 2010.

English translation of Russian Office Action regarding Russian Patent Application No. 2008120559, dated Mar. 15, 2010.

Office Action received in Japanese Patent Application No. 2008-537688 mailed Nov. 1, 2011.

Final Office Action for Japanese Patent Application No. 2008-537688, dated Apr. 24, 2012.

Korean Office Action for Patent Application No. 10-2008-7009931, dated Oct. 16, 2012 (English summary only).

Australian Office Action for Patent Application No. 2006306755, dated Sep. 4, 2012; 3 pages.

* cited by examiner

METHOD OF FORMING A NONWOVEN FABRIC AND FASTENING SYSTEM THAT INCLUDE AN AUTO-ADHESIVE MATERIAL

REFERENCE TO RELATED APPLICATION

This patent application is a divisional patent application of U.S. patent application Ser. No. 11/260,356, filed on Oct. 27, 2005, now U.S. Pat. No. 8,034,430 which is incorporated by reference in its entirety.

FIELD OF THE INVENTION

This invention relates to a nonwoven fabric, fastening system and method, and in particular to a nonwoven fabric, fastening system and method that include an auto-adhesive material.

BACKGROUND OF THE INVENTION

Many products include fastening systems that are used to join different items together, or different portions of the same item together. As an example, a fastening system is typically used to adhere different portions of a diaper together when a diaper is placed onto a child.

Some fastening systems are formed as an adhesive tape that includes a substrate which has a tacky material covering some (or all) of the substrate. The tacky material covers one or both sides of the substrate depending on the type of fastening system.

One drawback with using adhesive tapes to join items together is that the tapes readily stick to unwanted areas which make them cumbersome to handle. As an example, in some fastening systems that are used in diapers, the tacky material can undesirably stick to a child's tender skin.

Another drawback with using adhesive tapes is that the tacky material which is used in many adhesive tapes is easily contaminated (e.g., with dirt, baby powder, lotion, baby oil, etc.). The ability of an adhesive tape to effectively secure (and re-secure) items together is reduced as the tacky material becomes contaminated.

Some adhesive tapes try to minimize unwanted sticking and/or contamination of the tacky material by placing a temporary cover over the tacky material. One disadvantage of incorporating a cover for the tacky material is that the consumer needs to perform some labor in order to get the adhesive tape ready for fastening. In addition, the consumer needs to dispose of a cover once it is removed from the rest of the adhesive tape.

Another type of fastening system incorporates hook and loop type elements. These types of systems typically require the hook elements to be on one item (or section) so that they can be secured to the loop elements on another item (or section).

One drawback with using hook and loop type elements is that the hook and loop type elements can be abrasive if they engage items other than each other. As an example, when hook and loop type elements are used in diapers, the hook and loop type elements can undesirably abrade a child's tender skin. In addition, hook and loop type elements are often relatively stiff such that they are difficult to incorporate into many types of products.

Some types of fastening systems include an auto-adhesive tape or film. An auto-adhesive tape or film typically has self-adhesive properties such that auto-adhesive tapes or films are substantially non-adhesive with respect to many other materials. Some auto-adhesive tapes or films may be repeatedly adhered together and separated at service (e.g., room) temperature.

One of the advantages of auto-adhesive tapes or films is that they are useful in a variety of applications. As an example, auto-adhesive tapes may be especially well suited for many diaper-related applications because auto-adhesive tapes are not readily contaminated by materials that are commonly present in diaper changing environments (e.g., baby lotions, oils and powders). In addition, auto-adhesive tapes do not readily stick to unwanted areas or sections such that they are typically easier to handle.

There are some drawbacks associated with auto-adhesive tapes or films. One of the drawbacks is that they must be formed into tapes or films. The manufacturing process that is associated with fabricating an auto-adhesive tape or film can be relatively burdensome. In addition, there are times where it may be difficult to incorporate an elongated auto-adhesive tape or film into a consumer product.

Another drawback with auto-adhesive tapes or films is that they are relatively smooth such that it may be difficult to supplement the auto-adhesive capability of the tape or film with any type of mechanical attachment to the auto-adhesive tape or film. Auto-adhesive tapes or films typically do not include any auto-adhesive fibers or filaments such that it is difficult to adequately combine the auto-adhesive tapes or films with any type of hook and loop fastening system.

SUMMARY OF THE INVENTION

The present invention relates to a nonwoven fabric that includes a first web of extruded strands where at least some of the extruded strands include an auto-adhesive material. The nonwoven fabric is adapted to be bonded to another item that includes a similar auto-adhesive material.

The nonwoven fabric may be used to join one item to another item, or to join one portion of an item to another portion of the same item. As an example, different sections of the nonwoven fabric may be used to secure one portion of a diaper to another portion of a diaper.

As used herein, the term "auto-adhesive" refers to self-adhesive properties of a polymeric material. An auto-adhesive is substantially non-adhesive with respect to many other materials. Some auto-adhesives may be repeatedly adhered together and separated at service (e.g., room) temperature.

As used herein, the Peak Load of Auto-adhesive Strength represents a force that is required to separate a nonwoven fabric that is attached to itself. In some embodiments, the nonwoven fabric may exhibit a Peak Load of Auto-adhesive Strength value that is greater than about 100 grams per inch width of the nonwoven fabric.

In another form, the present invention relates to a method of forming a nonwoven fabric. The method includes extruding a plurality of strands where at least some of the strands are formed of an auto-adhesive material. The method further includes routing the plurality of strands toward a moving support and then depositing the plurality of strands onto the moving support. The method further includes stabilizing the plurality of strands to form a web.

In some embodiments of the method, routing the plurality of strands toward a moving support may include routing the plurality of strands through a spin pack. In addition, extruding a plurality of strands may include co-extruding a first component and a second component such that the auto-adhesive material is the first component and at least one other material is the second component.

In another form, the present invention relates to a fastening system. The fastening system includes a nonwoven fabric that has a web which is formed of a plurality of extruded strands where at least some of the strands include an auto-adhesive material. The fastening system further includes a foam layer that has a surface with a plurality of free-standing struts. At least some of the free-standing struts include an auto-adhesive material that is similar to the auto-adhesive material of the nonwoven fabric such that the free-stranding struts are adapted to engage at least a portion of the plurality of strands on the web.

In some embodiments of the fastening system, at least some of the plurality of strands that include an auto-adhesive material may form auto-adhesive loops that engage the auto-adhesive free-standing struts. In addition, at least a portion of some of the auto-adhesive free-standing struts may form auto-adhesive hooks such that the auto-adhesive hooks on the foam layer are adapted to engage the auto-adhesive loops on the web.

DESCRIPTION OF THE INVENTION

Figure 1:
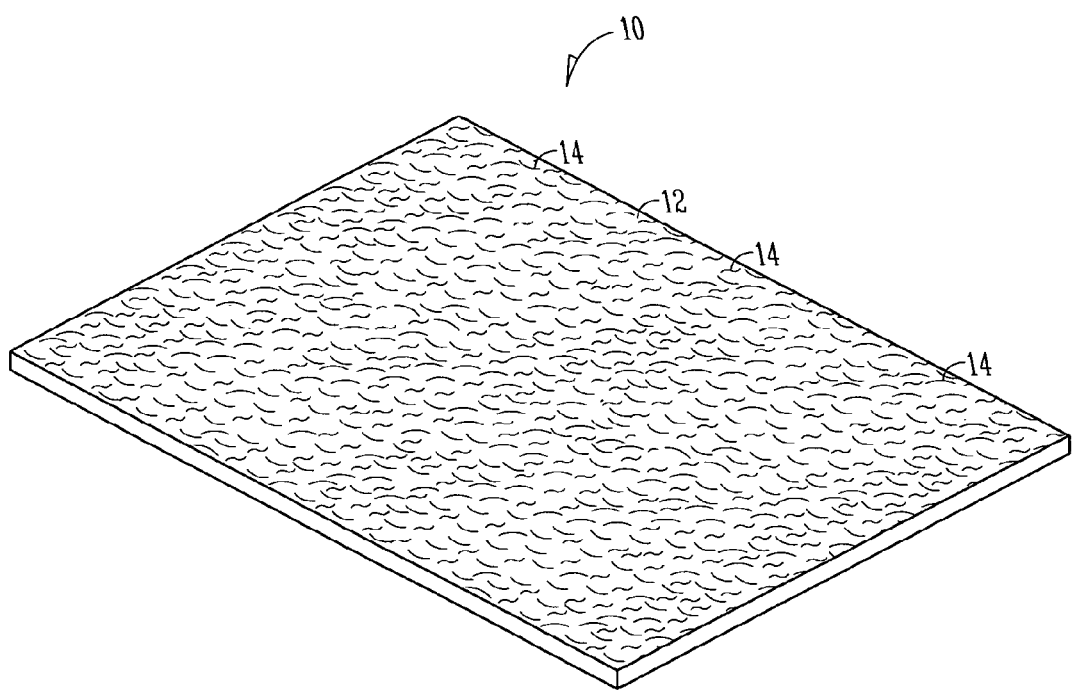
FIG. 1 is a perspective view illustrating an example nonwoven fabric.

FIG. 1 illustrates a nonwoven fabric 10 that includes a first web 12. The first web 12 is formed of extruded strands 14 that include an auto-adhesive material.

As used herein, nonwoven fabric refers to a web of material that has been formed without use of weaving processes that typically produce a structure of individual strands which are interwoven in a repeating manner. The nonwoven fabric may be formed by a variety of processes (e.g. meltblowing, spunbonding, film aperturing and staple fiber carding).

Although only a portion of the first web 12 is shown in FIG. 1, it should be noted that the first web 12 may be any size or shape. In addition, the first web 12 may be a variety of different thickness depending on the application where the nonwoven fabric 10 is used. The extruded strands 14 may be formed through any extrusion process that is known now or discovered in the future (e.g., meltblowing).

As used herein, the term "auto-adhesive" refers to self-adhesive properties of a material. An auto-adhesive is substantially non-adhesive with respect to many other materials. Some auto-adhesives may be repeatedly adhered together and separated at service (e.g., room) temperature.

In some embodiments, the auto-adhesive material may be a polymeric material that includes thermoplastic elastomers. As an example, the thermoplastic elastomers may have molecules that include sequential arrangements of unique combinations of monomer units. The thermoplastic elastomers should have relatively stable auto-adhesive properties and be substantially non-adhesive with respect to other materials.

In addition, the auto-adhesive material may include a thermoplastic elastomer that has physical cross-links which restrict the elastomer mobility (i.e., flow). Restricting the elastomeric mobility may promote the auto-adhesive properties of a thermoplastic elastomer.

Some example thermoplastic elastomers that may be used in the auto-adhesive material include multiblock copolymers of radial, triblock and diblock structures including non-rubbery segments of mono- and polycyclic aromatic hydrocarbons, and more particularly, mono- and polycyclic arenes. As examples, mono- and polycyclic arenes may include substituted and unsubstituted poly(vinyl)arenes of monocyclic and bicyclic structure.

In some embodiments, the thermoplastic elastomers may include non-rubbery segments of substituted or unsubstituted monocyclic arenes of sufficient segment molecular weight to assure phase separation at room temperature. As examples, monocyclic arenes may include polystyrene and substituted polystyrenes that have monomer units such as styrene and alkyl substituted styrene (e.g., alpha methylstyrene and 4-methylstyrene). Other examples include substituted or unsubstituted polycyclic arenes that have monomer units (e.g., 2-vinyl naphthalene and 6-ethyl-2-vinyl naphthalene).

It should be noted that the thermoplastic elastomers may also include rubbery segments that are polymer blocks which may be composed of homopolymers of a monomer, or a copolymer that includes two or more monomers selected from aliphatic conjugated diene compounds (e.g., 1,3-butadiene and isoprene). Some example rubbery materials include polyisoprene, polybutadiene and styrene butadiene rubbers. Other example rubbery materials include saturated olefin rubber of either ethylene/butylene or ethylene/propylene copolymers, which may be derived from the corresponding unsaturated polyalkylene moieties (e.g., hydrogenated polybutadiene and polyisoprene).

In addition, the thermoplastic elastomer may be part of a styrenic block copolymer system that includes rubbery segments which may be saturated by hydrogenating unsaturated precursors (e.g., a styrene-butadiene-styrene (SBS) block copolymer that has center or mid-segments which include a mixture of 1,4 and 1,2 isomers). As an example, a-butadiene-styrene (SBS) block copolymer that includes center or mid-segments which have a mixture of 1,4 and 1,2 isomers may be hydrogenated to obtain (i) a styrene-ethylene-butylene-styrene (SEBS) block copolymer; or (ii) a styrene-ethylene-propylene-styrene (SEPS) block copolymer.

In some embodiments, the auto-adhesive material may include a mixture of a polyethylene and a block copolymer. As an example, the auto-adhesive material may include a mixture of one or more block copolymers selected from the group consisting of poly(styrene)-co-poly(ethylene-butylene)-co-poly(styrene) copolymer, poly(styrene)-co-poly(ethylene-butylene) copolymer, and a polyethylene polymer. In some embodiments, the one or more block copolymers may be between about 30 weight percent to about 95 weight percent of the auto-adhesive material, and the polyethylene polymer may be between about 5 weight percent to about 70 weight percent of the auto-adhesive material (wherein all weight percents are based on the total weight amount of the block copolymer and the polyethylene polymer that are present in the auto-adhesive layer).

As used herein, the Peak Load of Auto-adhesive Strength represents a force that is required to separate the nonwoven fabric 10 when it is attached to itself. When the nonwoven fabric 10 is used as an adhesive component, the Peak load of Auto-adhesive Strength should meet the adhesive strength requirement for a particular application. If a nonwoven fabric 10 is used in a fastening system, the Peak Load of Auto-adhesive Strength for the nonwoven fabric 10 needs to be high enough to prevent the fastening system from opening during use. A nonwoven fabric 10 that exhibits too low of a Peak Load of Auto-adhesive Strength may not be suitable for some fastening system applications.

The nonwoven fabric 10 readily bonds to other items that include a similar auto-adhesive material with a strength that is greater than the strength which is generated when the nonwoven fabric 10 is bonded to any other type of material (e.g., a bonding strength that is at least twice as great). As an example, the nonwoven fabric 10 may exhibit a Peak Load of Auto-Adhesive Strength value that is greater than about 100 grams per inch width of the nonwoven fabric 10 (about 118 grams per centimeter width of the layer), and up to about 2000 grams per inch width of the nonwoven fabric 10 (about 787 grams per centimeter width of the layer). The method by which the Peak Load of Auto-Adhesive Strength value for a web is determined is set forth in U.S. Pat. No. 6,261,278 which is incorporated by reference herein.

The type of auto-adhesive material that is used to form the plurality of strands 14 will be selected based on (i) processing parameters; (ii) physical properties; (iii) packaging issues; and (iv) costs (among other factors). The first web 12 should have properties that are required for a particular product and/or process. The physical properties of the auto-adhesive material may be controlled to define properties for the nonwoven fabric 10 such as melting temperature, shear strength, crystallinity, elasticity, hardness, tensile strength, tackiness and heat stability (among other properties).

In some embodiments, the nonwoven fabric 10 may be made by melt spinning thermoplastic materials. This type of nonwoven fabric 10 may be referred to as a spunbond material.

Example methods for making spunbond polymeric materials are described in U.S. Pat. No. 4,692,618 to Dorschner et al., and U.S. Pat. No. 4,340,563 to Appel et al. both of which disclose methods for making spunbond nonwoven webs from thermoplastic materials by extruding the thermoplastic material through a spinneret and drawing the extruded material into filaments with a stream of high velocity air to form a random web on a collecting surface. U.S. Pat. No. 3,692,618 to Dorschner et al. discloses a process wherein bundles of polymeric filaments are drawn with a plurality of eductive guns by very high speed air while U.S. Pat. No. 4,340,563 to Appel et al. discloses a process wherein thermoplastic filaments are drawn through a single wide nozzle by a stream of high velocity air. Some other example melt spinning processes are described in U.S. Pat. No. 3,338,992 to Kinney; U.S. Pat. No. 3,341,394 to Kinney; U.S. Pat. No. 3,502,538 to Levy; U.S. Pat. No. 3,502,763 to Hartmann; U.S. Pat. No. 3,909,009 to Hartmann; U.S. Pat. No. 3,542,615 to Dobo et al., and Canadian Patent Number 803,714 to Harmon.

In some embodiments, desirable physical properties may be incorporated into the nonwoven fabric 10 by forming the strands 14 out of a multicomponent or bicomponent material where at least of one the materials in the bicomponent material is an auto-adhesive material. The auto-adhesive material may be similar to any of the auto-adhesive materials described above.

As used herein, strand refers to an elongated extrudate formed by passing a polymer through a forming orifice (e.g., a die). A strand may include a fiber, which is a discontinuous strand having a definite length, or a filament, which is a continuous strand of material.

Some example methods for making a nonwoven fabric from multicomponent or bicomponent materials are disclosed. U.S. Pat. No. 4,068,036 to Stanistreet, U.S. Pat. No. 3,423,266 to Davies et al., and U.S. Pat. No. 3,595,731 to Davies et al. disclose methods for melt spinning bicomponent filaments to form a nonwoven fabric. The nonwoven fabric 10 may be formed by cutting the meltspun strands into staple fibers, and then forming a bonded carded web, or by laying the continuous bicomponent filaments onto a forming surface and thereafter bonding the web.

Figure 2A:
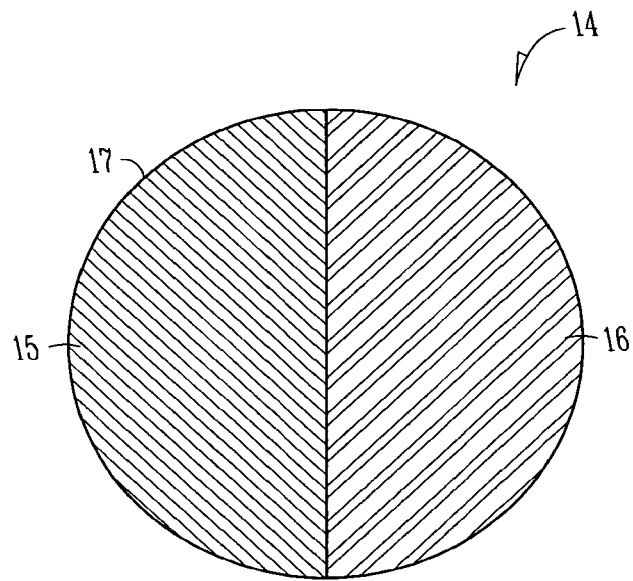
FIGS. 2A-2C are cross-section views illustrating example bicomponent strands that may be used in the nonwoven fabric shown in FIG. 1.
Figure 2B:
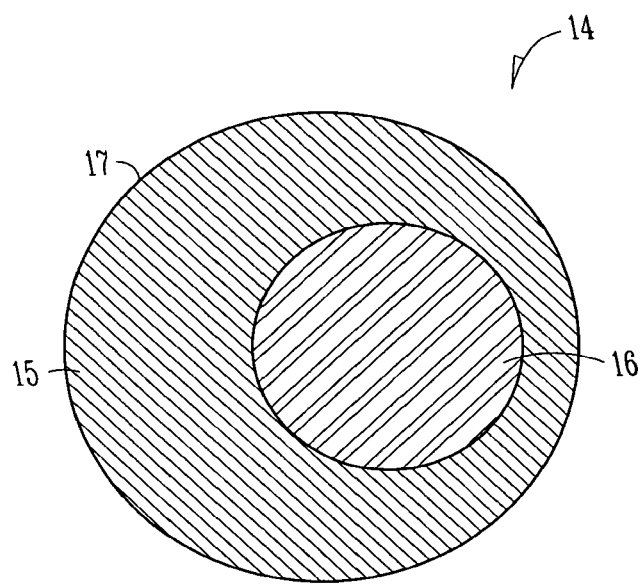
Figure 2C:
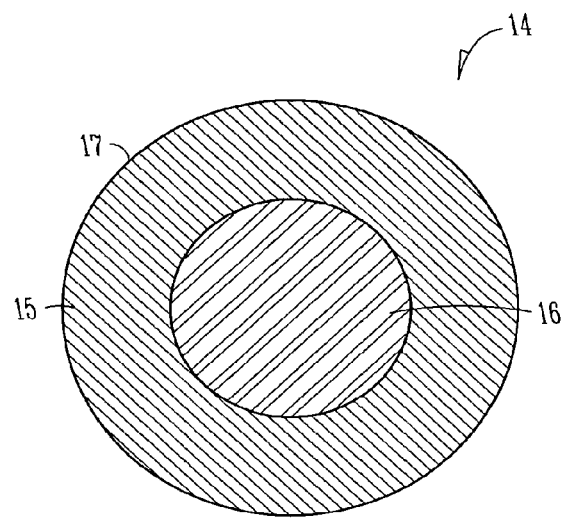

FIGS. 2A-2C illustrate some example forms of bicomponent strands 14 that may be used to form web 12. The strands 14 include a first component 15 and a second component 16 that are arranged in substantially distinct zones across the cross-section of the bicomponent strands 14 and extend along the length of the bicomponent strands 14. The first component 15 of the bicomponent strand includes an auto-adhesive material and constitutes at least a portion of the peripheral surface 17 on the bicomponent strands 14. Since the first component 15 exhibits different properties than the second component 16, the strands 14 may exhibit properties of the first and second components 15, 16.

The first and second components 15, 16 may be arranged in a side-by-side arrangement as shown in FIG. 2A. FIG. 2B shows an eccentric sheath/core arrangement where the second component 16 is the core of the strand 14 and first component 15 is the sheath of the strand 14. It should be noted that the resulting filaments or fibers may exhibit a high level of natural helical crimp in the sheath/core arrangement illustrated in FIG. 2B. In addition, the first and second components 15, 16 may be formed into a concentric sheath/core arrangement as shown in FIG. 2C.

Although the strands 14 are disclosed as bicomponent filaments or fibers, it should be understood that the nonwoven fabric 10 may include strands 14 which have one, two or more components. In addition, the nonwoven fabric 10 may be formed of single component strands that are combined with multicomponent strands. The type of materials that are selected for the first and second components 15, 16 will be based on processing parameters and the physical properties of the material (among other factors).

It should be noted the auto-adhesive material may include additives. In addition, when the strands 14 are formed of a bicomponent (or multicomponent) strands 14, some (or all) of components that form the strands 14 may include additives. As an example, the strands 14 may include pigments, antioxidants, stabilizers, surfactants, waxes, flow promoters, plasticizers, nucleating agents and particulates (among other additives). In some embodiments, the additives may be included to promote processing of the strands 14 and/or web 12.

Figure 3:
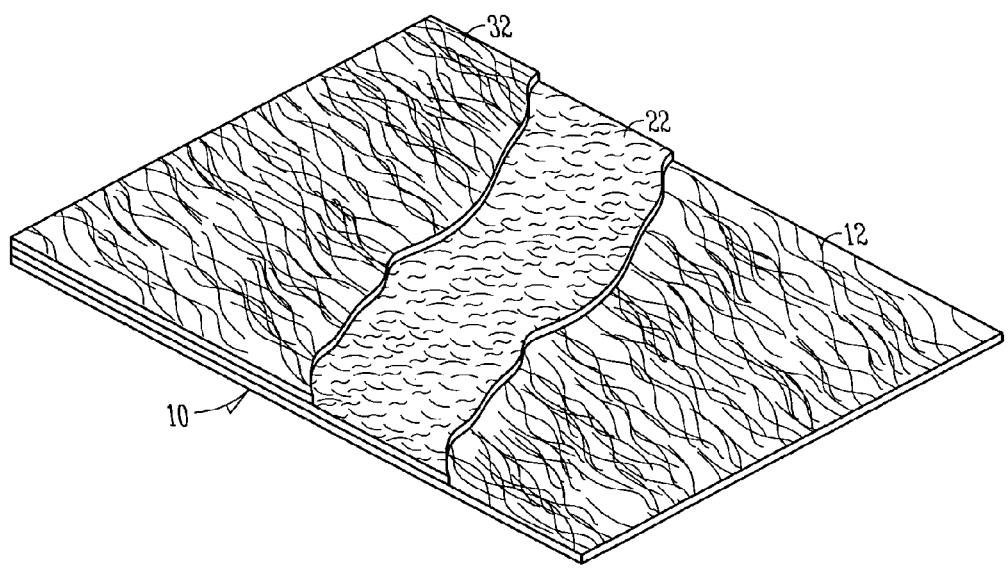
FIG. 3 is a perspective view illustrating another example nonwoven fabric.

As shown in FIG. 3, the nonwoven fabric 10 may be formed of multiple webs 12, 22, 32. The first web 12 of extruded strands 14 may be similar to first web 12 described above. The first web 12 may be bonded to a second web 22 of extruded strands 14 such that the first and second webs 12, 22 are positioned in laminar surface-to-surface relationship. In addition, the second web 22 may be bonded to a third web 32 such that the second and third webs 22, 32 are positioned in laminar surface-to-surface relationship.

In some embodiments, the second and/or third webs 22, 32 may be a spunbond material while in other embodiments the second and/or third webs 22, 32 may be made by meltblowing techniques. Some example meltblowing techniques are described in U.S. Pat. No. 4,041,203, the disclosure of which is incorporated herein by reference. U.S. Pat. No. 4,041,203 references the following publications on meltblowing techniques which are also incorporated herein by reference: An article entitled "Superfine Thermoplastic Fibers" appearing in INDUSTRIAL & ENGINEERING CHEMISTRY, Vol. 48, No. 8, pp. 1342-1346 which describes work done at the Naval Research Laboratories in Washington, D.C.; Naval Research Laboratory Report 111437, dated Apr. 15, 1954; U.S. Pat. Nos. 3,715,251; 3,704,198; 3,676,242; and 3,595,245; and British Specification No. 1,217,892.

Each of the second and third webs 22, 32 may have substantially the same composition as the first web 12 or have a different composition than the first web 12. In addition, the second and third webs 22, 32 may be formed from single component, bicomponent or multicomponent strands 14.

In some embodiments, the first, second and/or third webs 12, 22, 32 may formed separately and then bonded together (e.g., by thermal point bonding). It should be noted that when the first, second and possibly third web are bonded together, and a common elastomeric polymer is present in the strands 14 that form the first, second and third webs 12, 22, 32, the bonding between the first, second and third webs 12, 22, 32 may be more durable.

In other embodiments, the first, second and third webs 12, 22, 32 may be formed in a continuous process wherein each of the first, second and third webs 12, 22, 32 is formed one on top of the other. Both processes are described in U.S. Pat. No. 4,041,203, which has already been incorporated herein by reference.

The types of materials that are selected for the extruded strands 14 that make up the first, second and third webs 12, 22, 32 will be based on processing parameters and the desired physical properties of the nonwoven fabric 10 (among other factors). The first, second and third webs 12, 22, 32 may be attached together through any method that is known now or discovered in the future. Although the first, second and third webs 12, 22, 32 are partially shown as webs of the same size, it should be noted that the first, second and third webs 12, 22, 32 may be different sizes and/or shapes. In addition, the first, second and third webs 12, 22, 32 may be the same (or different) thicknesses.

A method of forming a nonwoven fabric 10 will now be described with reference to FIG. 4. The method includes extruding a plurality of strands 14 where at least some of the strands 14 are formed of an auto-adhesive material. The method further includes routing the plurality of strands 14 toward a moving support 66 and depositing the plurality of strands 14 onto the moving support 66. The method further includes stabilizing the plurality of strands 14 to form a web 12.

Figure 4:
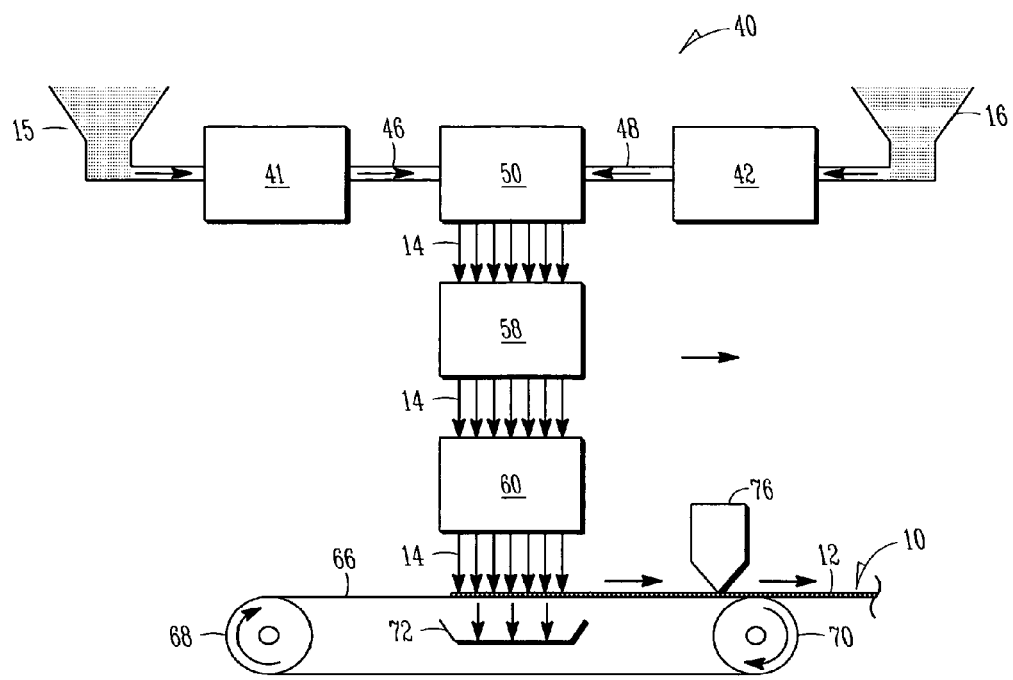
FIG. 4 is a side view of an example processing line that may be used to form a nonwoven fabric.

FIG. 4 shows an example processing line 40 that is arranged to produce a web 12 that includes a plurality of bicomponent continuous strands 14 (e.g., filaments or fibers). It should be understood that the processing line 40 may be adapted to form a nonwoven fabric 10 that includes one, two or multiple components in each strand 14. In addition, the processing line 40 may be adapted to form a nonwoven fabric 10 that include single component strands 14 in combination with multicomponent strands 14.

In the example embodiment that is illustrated in FIG. 4, the first and second components 15, 16 may be separately co-extruded in two different extruders 41, 42. It should be noted that the first and second extruders 41, 42 may be any extruder that is known now or discovered in the future.

In some embodiments, the first and second components 15, 16 are in the form of solid resin pellets (or particles) that are heated above their melting temperature and advanced along a path (e.g., by a rotating auger). The first component 15 is routed through one conduit 46 while the second component 16 is simultaneously routed through another conduit 48.

Both flow streams are directed into a spin pack 50 that initially forms the strands 14. As an example, the spin pack 50 may include a plate that has a plurality of holes or openings through which the extruded material flows. The number of openings per square inch in the spin pack 50 may range from about 5 to about 500 openings per square inch. The size of each opening in the spin pack may vary from about 0.1 millimeter (mm) to about 2.0 mm in diameter. It should be noted that the openings in the spin pack 50 may have a circular cross-section, or have a bilobal, trilobal, square, triangular, rectangular or oval cross-section depending on the properties that are desired for the nonwoven fabric 10.

In the example embodiment that is illustrated in FIG. 4, the first and second components 15, 16 may be directed into the spin pack 50 and then routed through the spin pack 50 in such a manner that the second component 16 forms a core while the first component 15 forms a sheath which surrounds the core. As discussed above with regard to FIGS. 2A-2C, the bicomponent strands 14 may have a side by side configuration or a core/sheath design (among other possible configurations).

One bicomponent strand 14 will be formed for each opening formed in the plate within the spin pack 50. Each of the plurality of strands 14 simultaneously exits the spin pack 50 at a first speed. The initial diameter of each bicomponent strand 14 will be dictated by the size of the openings that are in the plate of the spin pack 50.

In some embodiments, the plurality of strands 14 are routed downwardly through a quench chamber 58 to form a plurality of cooled strands 14. It should be noted that directing the strands 14 downward allows gravity to assist in moving the strands 14. In addition, the downward movement may aid in keeping the stands 14 separated from one another.

The strands 14 are contacted by one or more streams of air as the strands move into the quench chamber 58. The velocity of the incoming air may be maintained or adjusted so that the strands 14 are efficiently cooled.

The plurality of strands are then routed to a draw unit 60 that may be located below the quenching chamber 50 so as to again take advantage of gravity. As used herein, drawing involves subjecting the cooled strands 14 to pressurized air that draws (i.e., pulls) the molten strands 14 which are exiting the spin pack 50 downward.

The downward force that is generated by the pressurized air in the draw unit 60 causes the molten strands 14 to be lengthened and elongated. The amount that the diameter of the strands 14 is reduced depends upon several factors including (i) the number of molten strands 14 that are drawn; (ii) the distance over which the strands 14 are drawn; (iii) the pressure and temperature of the air that is used to draw the strands 14; and (iv) the spin line tension (among other factors).

The cooled strands 14 are pulled within the draw unit 60 at a speed that is faster than the speed at which the continuous molten strands 14 exit the spin pack 50. The change in speed causes the molten strands to be lengthened and reduced in cross-sectional area. The cooled strands 14 may be completely solid upon exiting the draw unit 60.

The solid strands 14 are deposited onto a moving support 66 after exiting the draw unit 60. As an example, the moving support 66 may be a continuous forming wire or belt that is driven by a drive roll 68 and revolves about a guide roll 70.

The moving support 66 may be constructed as a fine, medium or coarse mesh that has no openings or a plurality of openings. As examples, the moving support 66 may have a configuration that is similar to a standard window screen, or the moving support 66 may be tightly woven to resemble a wire that is commonly used by the paper industry in the formation of paper. A vacuum chamber 72 may be positioned below the moving support 66 to facilitate accumulation of the strands 14 onto the moving support 66.

In some embodiments, the strands 14 accumulate on the moving support 66 in a random orientation such that the accumulation of strands 14 at this point does not include any melt points or bonds that would stabilize the strands 14 into a web. The thickness and basis weight of the strands 14 is established in part by (i) the speed of the moving support 66; (ii) the number and diameter of the strands 14 that are deposited onto the moving support 66; and (iii) the speed at which the strands 14 are being deposited onto the moving support 66.

Depending on the type of processing line 40, the moving support 66 may rout the plurality of strands 14 under a hot air knife 76 that directs one or more streams of hot air onto the plurality of strands 14. The hot air needs to be of sufficient temperature to melt some of the strands 14 at points where the strands 14 contact, intersect or overlap other strands 14.

Figure 5:
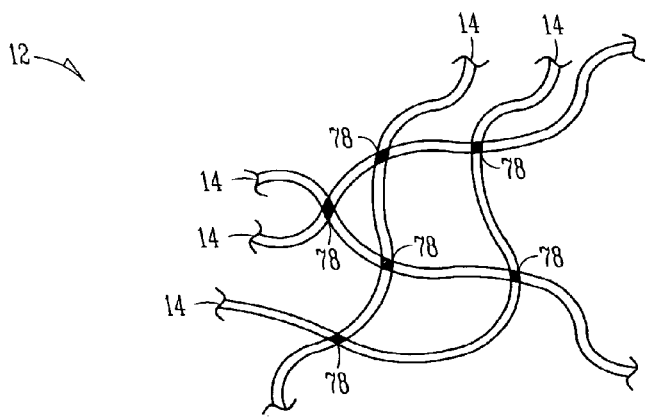
FIG. 5 is an enlarged view illustrating a portion of an example web that may be formed using the example processing line shown in FIG. 4.

As shown in FIG. 5, the strands 14 adhere to adjacent strands 14 at melt points 78 to form a stabilized web 12. The number of melt points 78 that form the web 12 is determined by a number of factors including: (i) the speed of the moving support 66; (ii) the temperature of the hot air; (iii) the types of material that are in the strands 14; and (iv) the degree to which the strands 14 are entangled (among other factors).

In some embodiments, the web 12 may be routed through a nip that is formed by a bond roll (not shown) and an anvil roll (not shown) which are heated to an elevated temperature. As an example, the bond roll may contain one or more protuberances that extend outward from the outer circumference of the bond roll. The protuberances may be sized and shaped to create a plurality of bonds in the web 12 as the web 12 passes through the bond roll and the anvil roll. Once the web 12 has bonds formed therein, the web 12 becomes a bonded web 12.

The exact number and location of the bonds in the bonded web 12 is determined by the position and configuration of the protuberances that are on the outer circumference of the bond roll. As an example, at least one bond per square inch may be formed in the bonded web 12, although embodiments are contemplated where the percent bonded area varies. As an example, the percent bonded area may be from about 10% to about 30% of the total area of the web 12.

Figure 6:
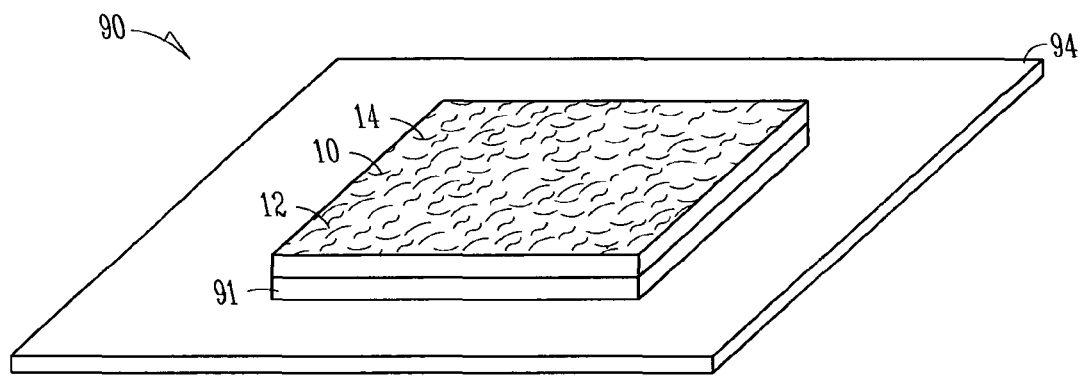
FIG. 6 is a perspective view illustrating an example fastening system.
Figure 7:
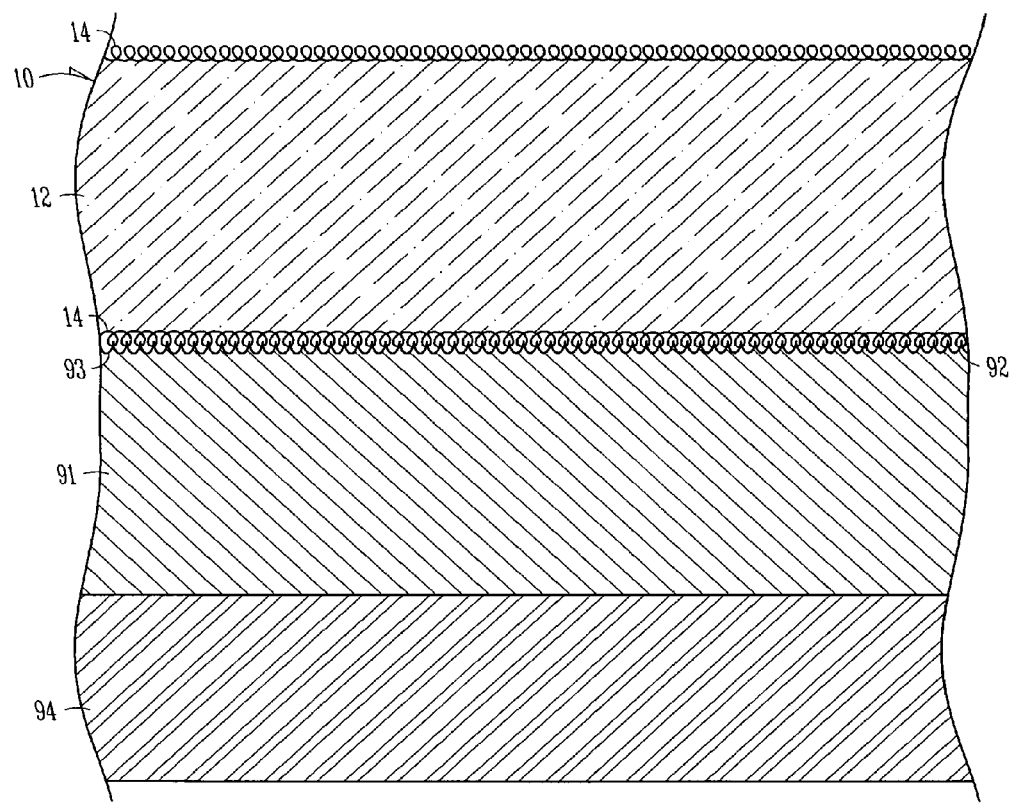
FIG. 7 is an enlarged side view of the example fastening system shown in FIG. 6.

FIGS. 6 and 7 depict a fastening system 90. The fastening system 90 includes a nonwoven fabric 10 that has a web 12 which is formed of a plurality of extruded strands 14 where at least some of the strands 14 include an auto-adhesive material. The fastening system 90 includes a foam layer 91 that has a surface 92 (see FIG. 7) which is formed of a plurality of free-stranding struts 93. The free-standing struts 93 are adapted to engage at least a portion of the plurality of strands 14 where at least some of the free-standing struts 93 include an auto-adhesive material that is similar to the auto-adhesive material of the nonwoven fabric 10.

It should be noted that the nonwoven fabric 10 may be similar to any of the nonwoven fabrics 10 that are described above. In addition, the foam layer 91 may be similar to any of the foam layers that are described in U.S. patent application Ser. No. 10/956,613 filed, Sep. 30, 2004 and European Patent 0235949A1. As an example, the foam layer 91 may be an open cell foam.

The auto-adhesive materials that are used in the respective nonwoven fabric 10 and foam layer 91 may be similar to any of the auto-adhesive materials described above. The types of auto-adhesive materials that are selected for the nonwoven fabric 10 and foam layer 91 that make up the fastening system 90 will be based on processing parameters and the desired physical properties of the fastening system 90 (among other factors).

In some embodiments, at least some of the plurality of strands 14 that include an auto-adhesive material may form auto-adhesive loops that engage the auto-adhesive free-standing struts 93 of the foam layer 91. In addition, at least a portion of some of the auto-adhesive free-standing struts 93 may form auto-adhesive hooks such that the auto-adhesive hooks are adapted to engage the auto-adhesive loops on the web 12.

It should be noted that the extent to which the strands 14 form loops and the free-standing struts 93 form hooks will depend in part on how the respective nonwoven fabric 10 and foam layer 91 are fabricated. As an example, the free-standing struts 93 may have diameters of about 500 microns or less.

In some embodiments, the foam layer 91 may be reinforced by attaching a support 94 to the foam layer 91. The support 94 may be attached to the foam layer 91 by any means (e.g., adhesive lamination of the support 94 to the foam layer 91 or formation of the foam layer 91 on the support 94). As an example, the support 94 may be dipped into a liquid that is cured to form the foam layer 91. U.S. Pat. No. 6,613,113, issued to Minick et al. on Sep. 2, 2003 describes such a process.

Adding the support 94 to the foam layer 91 may improve strength and/or flexibility of the foam layer 91. Improving the strength and flexibility of the foam layer 91 may increase the number of applications where the fastening system 90 may be used.

In some embodiments, the free-standing struts 93 of the foam layer 91 may be treated to have increased surface roughness which may facilitate attachment of the free-standing struts 93 to the nonwoven fabric 10. As an example, the free-standing struts 93 may be roughened by attaching particles to them (e.g., microspheres, mineral filler, etc.).

In other embodiments, the free-standing struts 93 may be etched or otherwise treated (e.g., by chemical attack, laser ablation, electron beam treatment, etc.) to remove portions of the surface material in individual free-standing struts 93. U.S. Pat. No. 3,922,455, issued to Brumlik et al. on Nov. 25, 1975 describes some examples of textured elements that may correspond to modified free-standing struts 93.

Figure 8:
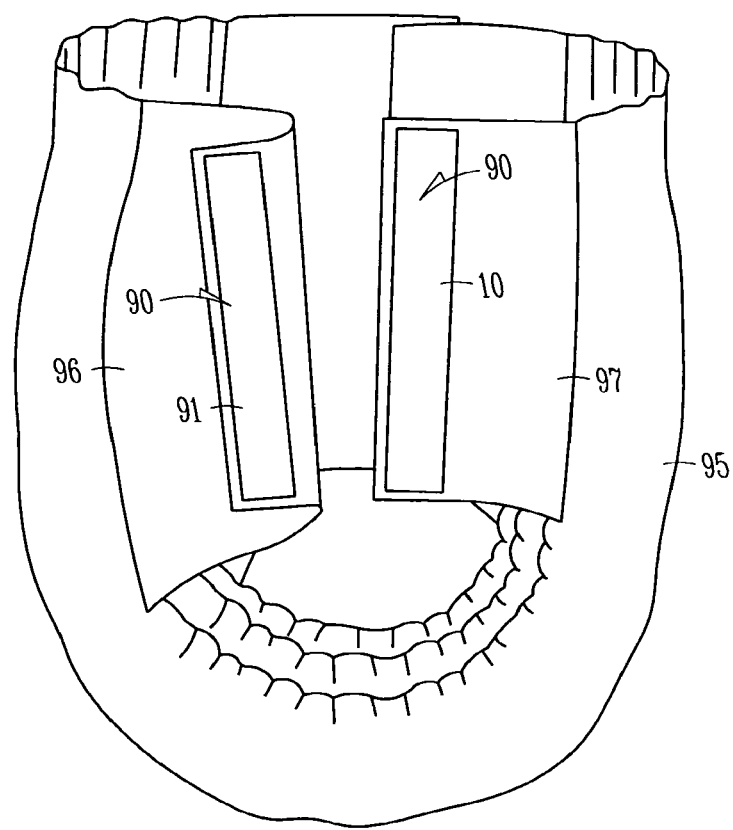
FIG. 8 illustrates an example absorbent article that includes the fastening system shown in FIG. 6.

FIG. 8 illustrates an example disposable absorbent article 95 (shown as a training pant) that may include any of fastening systems 90 described herein. The illustrated example absorbent article 95 is similar to the training pant disclosed in U.S. Pat. No. 6,562,167, issued to Coenen et al. on May 13, 2003 (which is incorporated herein by reference).

The example absorbent article 95 is illustrated in a partially fastened mode in FIG. 8. In the illustrated example embodiment, the foam layer 91 of the fastening system 90 is joined to front side panels 96 on the training pant 95 and a portion of the nonwoven fabric 10 is attached to rear panels 97 on the training pant 95. The fastening system 90 secures the training pant 95 about the waist of a wearer by engaging the nonwoven fabric 10 with the foam layer 91.

The nonwoven fabric 10 of the present invention may be useful in a variety of other applications. As examples, the nonwoven fabric 10 may incorporated into other products such as adult incontinent products, bed pads, other catamenial devices, sanitary napkins, tampons, wipes, bibs, wound dressings, surgical capes or drapes, soiled garment bags, garbage bags, storage bags and product packaging. The nonwoven fabric 10 may be especially well suited to diaper-related applications because the auto-adhesive material in the nonwoven fabric 10 is not readily contaminated with many of the materials that are commonly present in diaper changing environments (e.g., baby lotions, oils and powders).

The nonwoven fabric 10 may be secured to diapers (or other products) using thermal bonding and/or adhesives (among other techniques). As an example, one section of the nonwoven fabric 10 may be secured to one portion of a diaper such that the section is designed to engage another section of the nonwoven fabric 10 (e.g., a landing zone) on another portion of the diaper.

As part of fabricating any articles or products that include the nonwoven fabric 10, multiple sections may be cut from the first web 12 as the first web 12 is fed out from a continuous roll. The multiple sections may then be stacked for packaging or alternatively delivered as the continuous roll. In some forms, the multiple sections may be inter-folded, o-folded and/or compressed into various geometric shapes. In addition, the nonwoven fabric 10 may be embossed with logos, use instructions or any other design or information.

The nonwoven fabric 10 may also be decorative in color and/or shape depending on consumer appeal. There are also embodiments that are contemplated where the nonwoven fabric 10 has an unobtrusive product form such that the nonwoven fabric 10 does not interfere with the aesthetics of the products where the nonwoven fabric 10 is located.

While the invention has been described in detail with respect to specific embodiments, it will be appreciated that there are variations of, and equivalents to these embodiments. Accordingly, the scope of the present invention should be determined by the appended claims and any equivalents thereto.

What is claimed is:

1. A method of forming a nonwoven fabric, the method comprising:
   co-extruding a first component and a second component to form a plurality of strands, an auto-adhesive material being the first component and at least one other material being the second component;
   routing the plurality of strands toward a moving support;
   depositing the plurality of strands onto the moving support;
   stabilizing the plurality of strands to form a first web;
   forming a second web separate from the first web; and
   bonding the first web to the second web, wherein the first web and the second web have substantially the same composition.

2. The method of claim 1 wherein co-extruding a first component and a second component comprises co-extruding a first component and a second component such that the first component is formed on at least a portion of a periphery of each of the strands.

3. The method of claim 1 wherein co-extruding a first component and a second component comprises co-extruding a plurality of continuous filaments.

4. The method of claim 1 wherein co-extruding a first component and a second component comprises co-extruding a plurality of fibers.

5. The method of claim 1 wherein co-extruding a first component and a second component comprises meltblowing at least one of the first component and second component.

6. The method of claim 1 wherein co-extruding a first component and a second component comprises co-extruding a plurality of strands such that each of the strands is at least partially formed of an auto-adhesive material.

7. The method of claim 1 wherein routing the plurality of strands toward a moving support comprises routing the plurality of strands through a spin pack.

8. The method of claim 7 wherein the spin pack has from about 5 to about 500 openings per square inch.

9. The method of claim 7 wherein routing the plurality of strands through a spin pack comprises routing the plurality of strands to form a sheath/core arrangement, wherein the first component is a sheath of the strand and the second component is the core of the strand.

10. The method of claim 9 wherein routing the plurality of strands through a spin pack comprises routing the plurality of strands to form a concentric sheath/core arrangement.

11. The method of claim 7 wherein routing the plurality of strands through a spin pack comprises routing the plurality of strands such that the strands are arranged in a side-by-side arrangement.

12. The method of claim 7 wherein routing the plurality of strands toward a moving support comprises routing the plurality of strands through a quench chamber to cool the plurality of strands.

13. The method of claim 12 wherein routing the plurality of strands toward a moving support further comprises routing the plurality of strands through a draw unit to lengthen the cooled plurality of strands.

14. The method of claim 1 wherein routing the plurality of strands toward a moving support comprises routing the plurality of strands in a random orientation such that the plurality of strands do not include any melt points or bonds that would stabilize the strands into a web.

15. The method of claim 1 wherein routing the plurality of strands toward a moving support comprises routing the plurality of strands under a hot air knife that directs one or more streams of hot air onto the plurality of strands.

16. The method of claim 1 wherein stabilizing the plurality of strands to form a web comprises bonding the strands to one another.

* * * * *